United States Patent [19]

McIsaac et al.

[11] 4,276,235

[45] Jun. 30, 1981

[54] METHOD FOR PURIFYING BIDENTATE ORGANOPHOSPHOROUS COMPOUNDS

[75] Inventors: Lyle D. McIsaac, Blackfoot; Joseph F. Krupa, Idaho Falls; Norman C. Schroeder, Pocatello, all of Id.

[73] Assignee: The United States of America as represented by the United States Department of Energy, Washington, D.C.

[21] Appl. No.: 143,381

[22] Filed: Apr. 24, 1980

[51] Int. Cl.$^3$ .................... C07F 9/40; C01G 56/00
[52] U.S. Cl. .................... 260/990; 423/12
[58] Field of Search .................... 260/990

[56] References Cited

U.S. PATENT DOCUMENTS

| 3,993,729 | 11/1976 | Epstein et al. | 423/184 |
| 4,051,203 | 9/1977 | Schulz | 260/990 |

OTHER PUBLICATIONS

Krupa et al, ICP-1181, Preparee Under DOE contract EY-76-C-07-1540.
McIassac et al, "Flowsheet Dev. Work at the ICP plant, etc", distributed at Acetinide Symp. Pac. Conf. Honolulu, Hawaii about 04/01/79.
McIassaac et al.,, ICP-118- prepared under DOE contract DE AC07-761 DO 1540.

*Primary Examiner*—Anton H. Sutto
*Attorney, Agent, or Firm*—James W. Weinberger; Richard G. Besha; James E. Denny

[57] ABSTRACT

Bidentate organophosphorous compounds are purified of undesirable impurities by contacting a solution of the compounds with a mercuric nitrate solution to form an insoluble mercuric bidentate compound which precipitates while the impurities remain in solution. The precipitate is washed and then contacted with a mixture of an aqueous solution of a strong mercuric ion complexing agent and an organic solvent to complex the mercuric ion away from the bidentate compound which then dissolves in the solvent. The purified bidentate compounds are useful for extracting the actinide elements from aqueous acidic nuclear waste solutions.

5 Claims, No Drawings

METHOD FOR PURIFYING BIDENTATE ORGANOPHOSPHOROUS COMPOUNDS

CONTRACTUAL ORIGIN OF THE INVENTION

The United States Government has rights in this invention pursuant to Contract No. DE-AC07-76IDO1540 between the U.S. Department of Energy and Allied Chemical Corporation.

BACKGROUND OF THE INVENTION

The present invention relates to a method for the purification of bidentate organophosphorous compounds. More specifically the invention relates to a method for purifying bidentate organophosphorous compounds such as dihexyl N,N-diethylcarbamylmethylenephosphonate by mercury precipitation.

Solvent extraction processes which employ bidentate organophosphorous extractants are presently being actively developed by U.S. Department of Energy facilities at Hanford, Washington and Idaho Falls, Idaho for the removal and recovery of the antinide elements, particularly americium and plutonium, from nitric acid waste solutions generated at these sites. In general bidentate organophosphorous compounds are efficient extractants for trivalent, tetravalent, and hexavalent actinides which are present in aqueous acidic nuclear waste solutions. With the bidentate extractant, essentially all actinide values, e.g. AM (III), Cm (III), Pu (IV), Np (IV) and U (VI) are extracted into the organic phase and, thereafter, the actinides are stripped from the organic by contact with dilute aqueous acidic or alkaline solutions. U.S. Pat. No. 3,993,729, issued Nov. 23, 1976 and assigned to the common assignee describes the application of bidentate organophosphorous extractants and actinide removal schemes from various acid nuclear fuel reprocessing solutions such as those generated in the Purex process.

Currently, preferred bidentate extractants are dihexyl-N,N-diethylcarbamylmethylenephosphonate hereinafter referred to as DHDECMP, and dibutyl-N,N-diethylcarbamylmethylenephosphonate, hereinafter referred to as DBDECMP. These extractants and other neutral bidentate organophosphorous compounds are generally available as crude products (about 65% pure) which contain various impurities. The actinides are irreversibly extracted from acidic waste solutions using crude DHDECMP as the extractant. The actinides are readily stripped from purified DHDECMP using dilute nitric acid which contains hydroxylamine nitrate to reduce plutonium to valence (III). Thus, DHDECMP or DBDECMP must be purified to permit the use of low acid solutions to strip actinides from these extractants.

Present methods for purifying the commercially available DHDECMP and DBDECMP from the unknown impurities include vacuum distillation, liquid chromatography and hydrolysis of impurities at 60° C. with a 6 M HCl solution. Another method for purifying the bidentate organophosphorous compounds is described in U.S. Pat. No. 4,051,203, which issued Sept. 27, 1977 and is assigned to the common assignee. As described herein, the bidentates in an organic solvent are purified by a contact with ethylene glycol which perferentially extracts the impurities away from the solvvent solution.

However, all of these purification procedures have disadvantages. Specialized vacuum distillation and liquid chromatography equipment is expensive and DHDECMP or DBDECMP obtained from these methods cost more than twice as much as the technical grade material. Specialized corrosion resistant equipment is needed to perform HCl hydrolysis of impurities present in the crude bidentate extractants, and more importantly the HCl also attacks the bidentates as well as the impurities. The use of ethylene glycol for purification does not seem to produce a product that has all of the desirable extraction characteristics. Therefore, there remains a need for a simple, reliable and effective purification process which can be carried out economically and easily with conventional equipment.

SUMMARY OF THE INVENTION

A simple and effective process has been developed for the removal of impurities from technical grade bidentate organophosphorous compounds. By the process of the invention, the bidentate organophosphorous compounds are dissolved in a water-immiscible organic solvent to form a solvent solution, the organic solvent being one in which the mercuric bidentate compound to be formed is insoluble, the solution is then contacted with an aqueous acidic mercuric nitrate solution whereby mercury reacts with the bidentate to form an insoluble mercuric bidentate compound which precipitates out while the impurities remain in solution. The precipitate is separated from the aqueous and organic solutions and contacted with a bidentate recovery solution, which is a mixture of an aqueous solution of a strong mercuric ion complexing agent and a water-immiscible organic solvent, whereby the mercuric ion is complexed from the insoluble mercuric bidentate compound, re-forming the soluble bidentate compound which then dissolves in the organic solvent, thereby purifying the bidentate organophosphorous compound. The purified bidentate compound can then be readily recovered from the organic solvent.

Using the method of the invention, it is possible to obtain bidentate compounds which are greater than 95% pure at a yield of greater than 85%.

It is therefore one object of the invention to provide an improved method for purifying commercially available bidentate organophosphorous compounds.

It is another object of the invention to provide an improved method for removing the undesirable impurities from commercially available bidentate organophosphorous compounds.

Finally, it is the object of the invention to provide a simple and effective method for preparing highly purified DHDECMP and DBDECMP from the technical grade material in order to improve the compounds for the extraction of actinides from acidic nuclear waste.

DESCRIPTION OF THE PREFERRED EMBODIMENT

These and other objects of the invention may be met by diluting the DHDECMP or DBDECMP to about 20 volume percent (v/v) in a water-immiscible organic solvent such as hexane, to form a solvent solution, contacting the solution with about an equal volume of an aqueous nitric acid solution containing about 1 M mercuric nitrate at 40° C., for a period of time sufficient for the mercuric ion to react with the bidentate compound to form an insoluble mercuric bidentate compound which precipitates out, while the impurities remain in the solvent solution, separating the precipitate from the aqueous and the organic solutions, washing the precipitate with a mixture of organic solvent and water to remove any entrained impurities, contacting the precipitate with a bidentate recovery solution, the recovery solution consisting of a mixture of an aqueous solution containing about 0.5 M Na$_2$CO$_3$ and about 2 M KCN and a water-immiscible organic solvent such as hexane whereby the mercuric ion is complexed from the insoluble mercuric bidentate compound re-forming the soluble bidentate compound which dissolves in the organic solvent, separating the organic solvent from the aqueous solution and recovering the purified bidentate compound from the solvent.

The organic solvent may be any organic solvent which is water-immiscible, in which the bidentate organophosphorous compounds are soluble and in particular, one in which the mercuric bidentate compound is insoluble. Suitable solvents would include the aliphatic hydrocarbons of C$_5$ or more such as hexane or octane, kerosene or petroleum ether and some cyclic aliphatic hydrocarbons such as cyclohexane and decahydronaphthalene. Insolubility of the precipitate in the solvent is important because major product losses can occur due to the solubility of the precipitate in the solvent. The concentration of the bidentate compounds in the solvent may vary from about 10 to about 30 volume percent (v/v) with about 20 volume percent preferred. Loss of product may occur at the higher concentrations and particularly at concentrations over 30% v/v due to the solubility of the mercuric bidentate compounds in the impurities in the technical grade bidentate compounds.

The aqueous acidic solution of mercuric nitrate must contain sufficient mercuric ion to react stoichiometrically on a one to one mole ratio with the bidentate compound present in the solvent solution. Thus, the solution may contain any convenient concentration of mercuric nitrate for example 0.1 to 2.0 molar. To ensure complete precipitation and to account for any side reactions which may occur, a ratio of at least 1.5:1 mercuric ion to bidentate compound is preferred while higher ratios are also satisfactory. The nitric acid is present to solubilize the mercuric nitrate and may vary from about 0.05 M to 1.0 M HNO$_3$ or higher since the reaction appears to display no acid dependency, and since distribution coefficients have shown no difference over this acid range.

The temperature may vary from about 25° C. to 40° C. with the higher temperature being preferred in order to complete precipitation within a reasonable period of time. Reactions conducted at room temperature may take several hours to completely react the mercuric ion and bidentate and form the precipitate, while at 40° C. the reaction is essentially complete within about 1 hour. Temperatures higher than about 40° C. are to be avoided due to possible degradation of the bidentate compounds in the presence of acid at these higher temperatures. Times are not critical, only that it be sufficient to ensure complete precipitation of the bidentate compound present in the solvent mixture.

After formation of the precipitate is complete, it may be separated from the organic solvent in the aqueous solution by any convenient method known to those skilled in the art such as filtering, vacuum filtering or centrifugation. The recovered precipitate is then preferably washed several times with equal volumes of organic solvent and water to remove any entrained impurities. If washings are insufficient, recrystallization from a 20% benzene-80% hexane may also be used to free the precipitate from entrained impurities.

The bidentate recovery solution consists of a mixture of an aqueous solution of a mercuric ion complexing agent and an amount of water-immiscible organic solvent sufficient to dissolve the bidentate compound. The complexing agent can be any water soluble compound which is strong enough to complex the mercuric ion away from the bidentate compound. A solution of 0.5 M sodium carbonate containing 2 M potassium cyanide has been found satisfactory as a mercury complexing agent although other mercury complexants such as cysteine or chemical reduction by lithium amalgam may be just as satisfactory. The solution must be sufficiently caustic to drive the reaction in the right direction. The water-immiscible organic solvent may be any of the solvents which are satisfactory for preparing the the solvent mixture. Preferably the solvent is volatile in order to permit rapid evaporation of the solvent away from the bidentate compounds. A solvent which has been found to to be particularly suitable is hexane.

By the method of the invention for purifying the organophosphorous bidentate compounds, it is possible to obtain DHDECMP which is greater than 95% pure with a yield of about 85%.

While the method of the invention was developed especially for the purification of DHDECMP and DBDECMP, the process should be equally suitable for the purification of any of the bidentate organophosphorous compounds.

EXAMPLE I 18.1 ml of crude DHDECMP (65% pure) was dissolved in sufficient hexane to prepare a 20% solution of the solvent mixture. This mixture was reacted with an equal volume of 1 M Hg(NO$_3$)$_2$-1 M HNO$_3$ solution for one hour at 40° C. to form the mercury bidentate compound as a precipitate. After the solution was cooled to room temperature, it was centrifuged and the organic and aqueous phases discarded. The white amorphous precipitate was washed twice with a 90 ml solution of hexane and water (45 ml of each); centrifuging after each wash. Alternatively, the precipitate can be collected by vacuum filtration and washed with equal volumes of hexane and water. If washings are inefficient, recrystallization from 17 ml of 20% benzene-80% hexane solution may be used to free the precipitate from entrained impurities. The DHDECMP was regenerated by contacting the precipitate with a bidentate recovery solution consisting of 55 ml of 0.5 M Na$_2$CO$_3$-2 M KCN solution for 30 minutes; 25 ml of hexane being added to dissolve the liberated DHDECMP. The hexane-DHDECMP phae was then contacted with 15 ml of fresh sodium carbonate-cyanide solution for 15 minutes to ensure complete mercury complexing. The organic phase was then washed with equal volumes of water several times until neutral. (Complete removal of mercury was checked by acidifying a portion of the organic phase with 1 M HNO$_3$. A copper bead was then added to the acidifed organic phase to see if any mercury plates out. If positive, more cyanide washings are necessary.) After centrifuging, the organic phase was filtered and the hexane removed under a slight vacuum using a rotary evaporator. The recovered product was clear and colorless with a purity of greater than 95%, generally about 97%. Product recovery totalled about 85%. Impurities present were approximately equal amounts of dihexyl hexylphosphonate and the octyl, hexyl homolog of DHDECMP.

EXAMPLE II

To determine the overall yields of bidentate compound from various concentrations of the crude material in hexane, a series of examples were run in a manner similar to Example I. The results are shown in Table I below:

TABLE I

Overall Yields of DHDECMP vs % Crude DHDECMP in Hexane[a]

| % Crude DHDECMP | Yield (%) |
|---|---|
| 10 | 74 |
| 20 | 81 (85,86,86)[b] |
| 30 | 74 |

[a]Precipitation reaction at 40° C. for 1 hour with 1M Hg(NO$_3$)$_2$ — 0.1M HNO$_3$
[b]Precipitation reaction at 40° C. for 1 hour with 1M Hg(NO$_3$)$_2$ — 1.0M HNO$_3$ Since recovery of DHDECMP is 98% for the caustic cyanide step, the overall yield in Table I indicates that major losses are due to solubility of the mercuric bidentate compound in the organic phase.

It can be seen that the method of this invention provides an economical and effective method for purifying technical grade bidentate extractants to provide high purity bidentates which are satisfactory for use as actinide extractants.

The embodiments of this invention in which an exclusive property or privilege is claimed are defined as follows:

1. A method for removing impurities present in bidentate organophosphorous compounds comprising: dissolving the bidentate compound in a water-immiscible organic solvent to form a solvent solution containing up to 30 volume percent of the bidentate compound, the organic solvent being one in which the mercuric bidentate compound to be formed is insoluble and which is selected from the group consisting of aliphatic hydrocarbons of five or more carbon atoms and cyclic aliphatic hydrocarbons, contacting the solvent solution at a temperature of up to 40° C. with an aqueous nitric acid solution of mercuric nitrate containing sufficient mercuric ion and for a period of time sufficient from the mercuric ion to react with the bidentate compound to form an insoluble mercuric bidentate compound, which precipitates while the impurities remain in solution, separating the precipitate from the aqueous and the organic solutions, contacting the precipitate with a bidentate recovery solution, the recovery solution being a mixture of an aqueous solution of a strong mercuric ion complexing agent selected from the group consisting of potassium cyanide and cysteine and a water-immiscible organic solvent selected from the group consisting of aliphatic hydrocarbons of five or more carbon atoms and cyclic aliphatic hydrocarbons, whereby the mercuric ion is complexed from the insoluble mercuric bidentate compound reforming the soluble bidentate compound which dissolves in the organic solvent, separating the organic solvent from the aqueous solution, and recovering the purified bidentate solution.

2. The method of claim 1 wherein the aqueous acidic solution is from 0.05 to 1.0 M in HNO$_3$ and the mole ratio of mercuric ion to bidentate compound is at least 1:1.

3. The method of claim 3 wherein the aqueous acidic solutions is from 0.1 to 2.0 molar in mercuric nitrate and from 0.05 to 1.0 molar in nitric acid.

4. The method of claim 3 wherein the organic solvent is a member of the group consisting of hexane, octane, kerosene, petroleum ether, cyclohexane and decahydronophthalene.

5. The method of claim 4 wherein the aqueous solution of a strong mercuric ion complexing agent is a caustic solution containing potassium cyanide.

* * * * *